United States Patent
Toriumi et al.

(10) Patent No.: US 8,605,284 B2
(45) Date of Patent: Dec. 10, 2013

(54) MEASUREMENT DEVICE AND MEASUREMENT METHOD

(75) Inventors: Yoichi Toriumi, Tokyo (JP); Hideo Kawabe, Saitama (JP); Kenichi Kabasawa, Saitama (JP); Tatsuya Suzuki, Kanagawa (JP); Hirokazu Imai, Chiba (JP); Masatoshi Ueno, Kanagawa (JP)

(73) Assignee: Sony Corporation, Tokyo (JP)

( * ) Notice: Subject to any disclaimer, the term of this patent is extended or adjusted under 35 U.S.C. 154(b) by 181 days.

(21) Appl. No.: 13/228,921

(22) Filed: Sep. 9, 2011

(65) Prior Publication Data

US 2012/0069343 A1 Mar. 22, 2012

(30) Foreign Application Priority Data

Sep. 16, 2010 (JP) ................. 2010-208337

(51) Int. Cl.
*G01N 21/47* (2006.01)
*G01N 21/55* (2006.01)

(52) U.S. Cl.
USPC .......................................... 356/446; 356/445

(58) Field of Classification Search
USPC ................... 356/445–448, 612, 237.1–237.5; 362/245, 231, 240–241; 353/94, 31, 353/99; 250/559.34, 559.08, 559.2
See application file for complete search history.

(56) References Cited

U.S. PATENT DOCUMENTS

| | | | |
|---|---|---|---|
| 6,118,524 A * | 9/2000 | King et al. | 356/237.1 |
| 6,122,048 A * | 9/2000 | Cochran et al. | 356/239.4 |
| 6,207,946 B1 * | 3/2001 | Jusoh et al. | 250/208.1 |
| 6,947,151 B2 * | 9/2005 | Fujii et al. | 356/612 |
| 7,019,826 B2 * | 3/2006 | Vook et al. | 356/237.1 |
| 7,336,197 B2 * | 2/2008 | Ding et al. | 340/815.45 |
| 7,506,985 B2 * | 3/2009 | Radominski et al. | 353/94 |
| 7,557,920 B2 * | 7/2009 | Lebens | 356/394 |
| 8,144,968 B2 * | 3/2012 | Vodanovic | 382/141 |
| 8,208,148 B2 * | 6/2012 | Lengsfeld et al. | 356/445 |
| 2003/0109791 A1 * | 6/2003 | Kondo et al. | 600/500 |
| 2003/0231494 A1 * | 12/2003 | Shimokawa et al. | 362/245 |
| 2010/0156302 A1 * | 6/2010 | Park et al. | 315/151 |

FOREIGN PATENT DOCUMENTS

JP 2007-532183 11/2007

* cited by examiner

*Primary Examiner* — Sang Nguyen
(74) *Attorney, Agent, or Firm* — K&L Gates LLP

(57) ABSTRACT

A measurement device includes a light sensing element on which light from a measurement target region placing a measurement target thereon forms an image, and a plurality of light emitting elements that are disposed around the light sensing element and radiate light to the measurement target region, wherein the plurality of light emitting elements are disposed to be tilted with respect to the normal line of the measurement target region such that the central line of radiated emission from each of the light emitting elements passes through a substantial center of the measurement target region.

22 Claims, 12 Drawing Sheets

MEASUREMENT DEVICE AND MEASUREMENT METHOD

CROSS REFERENCES TO RELATED APPLICATIONS

The present application claims priority to Japanese Priority Patent Application JP 2010-208337 filed in the Japan Patent Office on Sep. 16, 2010, the entire contents of which are hereby incorporated by reference.

BACKGROUND

The present application relates to a measurement device and a measurement method.

In recent years, a spectrometry method has been proposed in which a measurement target is analyzed by irradiating the measurement target with light and measuring reflection light from the measurement target. In the spectrometry method, an optical device called an integrating sphere is used in many cases, in order to collect light without leakage of the reflection light from the measurement target. In the spectrometry method using the integrating sphere, there are the following two measurement procedures when largely classified.

(1) Irradiation light from light emitting elements are collected from multiple angles with respect to a measurement target, reflection light is collimated before a spectral filter and guided, and then spectral reflectance of the measurement target is measured.

(2) Diffuse reflection from a measurement target is collected at a spectral filter from multiple angles, reflection light is collimated before the spectral filter and guided, and then spectral reflectance of the measurement target is measured.

In addition, a method is generally performed in which a white light source such as a xenon lamp irradiates a measurement target with irradiation light, and reflection light from the measurement target is dispersed into several tens of wavelengths by a spectral filter.

Further, for example, as disclosed in Japanese Unexamined Patent Application Publication (Translation of PCT Application) No. 2007-532183, there has been proposed a spectrometry device which measures light from a measurement target without using the integrating sphere.

SUMMARY

However, the spectrometry device using the above-described integrating sphere has a problem in that since the integrating sphere or an optical element for collimating reflection light is necessary, the device is difficult to miniaturize. In addition, there are problems in that since it is necessary to supply a large amount of power to the xenon light source used as an irradiation light source emitting light, it is difficult to conserve electric power, and since spectral filters corresponding to several tens of wavelengths are necessary, it is difficult to reduce costs.

Even in the method disclosed in Japanese Unexamined Patent Application Publication (Translation of PCT Application) No. 2007-532183, since light from a measurement target is dispersed using a diffraction grating, the overall device is difficult to miniaturize.

It is desirable to provide a measurement device and a measurement method capable of further minimizing a device.

According to an embodiment, there is provided a measurement device including a light sensing element on which light from a measurement target region placing a measurement target thereon forms an image; and a plurality of light emitting elements that are disposed around the light sensing element in a ring shape and radiate light to the measurement target region, wherein the plurality of light emitting elements are disposed to be tilted with respect to the normal line of the measurement target region such that the central line of radiated emission from each of the light emitting elements passes through a substantial center of the measurement target region.

An angle formed by the central line of the radiated emission and the normal line of the measurement target region may be set according to a separation distance between the measurement target region and the light sensing element.

If the separation distance is equal to or less than a predetermined threshold value, the angle may be set to 45°, and if the separation distance exceeds the predetermined threshold value, the angle may be set to be less than 45°.

The measurement target region is preferably provided to face the light sensing element.

It is preferable that 4N (where N is an integer equal to or more than 1) light emitting elements be disposed around the light sensing element at an interval of (90/N)°.

A numerical aperture of the radiated emission which is preferably provided to the measurement target region is equal to or less than 0.2.

The plurality of light emitting elements may radiate light having the same wavelength characteristic.

The light emitting elements which radiate light having different N wavelengths may be disposed by four for each wavelength as the plurality of light emitting elements.

Twenty light emitting elements which radiate light having different 5 wavelengths may be disposed around the light sensing element at an interval of 18°.

The light having the different 5 wavelengths preferably has 500 nm, 540 nm, 580 nm, 620 nm, and 660 nm, respectively, as a central wavelength.

The full width at half maximum of the light having 580 nm as the central wavelength is preferably smaller than the full width at half maximum of the light having 500 nm, 540 nm, 620 nm, and 660 nm as the central wavelength.

The light emitting elements which radiate the light having the different N wavelengths may radiate the light in a time divisional manner so as to have a predetermined pulse width using N pulses.

The plurality of light emitting elements may respectively and simultaneously radiate white light so as to have a predetermined pulse width.

A light sensing surface of the light sensing element may be divided into N regions, and an optical filter which transmits light having different N wavelengths therethrough may be provided at an upper side of each of the regions.

The light sensing surface of the light sensing element may be divided into five regions, and the optical filters may transmit light having 500 nm, 540 nm, 580 nm, 620 nm, and 660 nm as a central wavelength therethrough.

The full width at half maximum of the light having 580 nm as the central wavelength is preferably smaller than the full width at half maximum of the light having 500 nm, 540 nm, 620 nm, and 660 nm as the central wavelength.

Collimated diffuse reflection from the measurement target region may be incident to the optical filters.

The size of the measurement target region may be substantially the same as the size of a spot formed by light radiated from the plurality of light emitting elements.

The measurement device may be disposed inside a casing at which an opening portion is provided, and the measurement target region may be a human skin surface placed on the opening portion.

According to another embodiment, there is provided a measurement method including radiating light of a predetermined wavelength from a plurality of light emitting elements which are disposed around a light sensing element in a ring shape on which light from a measurement target region placing a measurement target thereon forms an image, and which radiate light to the measurement target region, such that the central line of radiated emission from each of the light emitting elements passes through a substantial center of the measurement target region; and causing the light sensing element to sense diffuse reflection light from the measurement target region.

As described above, according to the present application, it is possible to further miniaturize a device in the measurement device which measures reflection light from a measurement target.

Additional features and advantages are described herein, and will be apparent from the following Detailed Description and the figures.

DETAILED DESCRIPTION

Embodiments of the present application will be described below in detail with reference to the drawings.

Further, the description will be made in the following order.

Figure 1A:
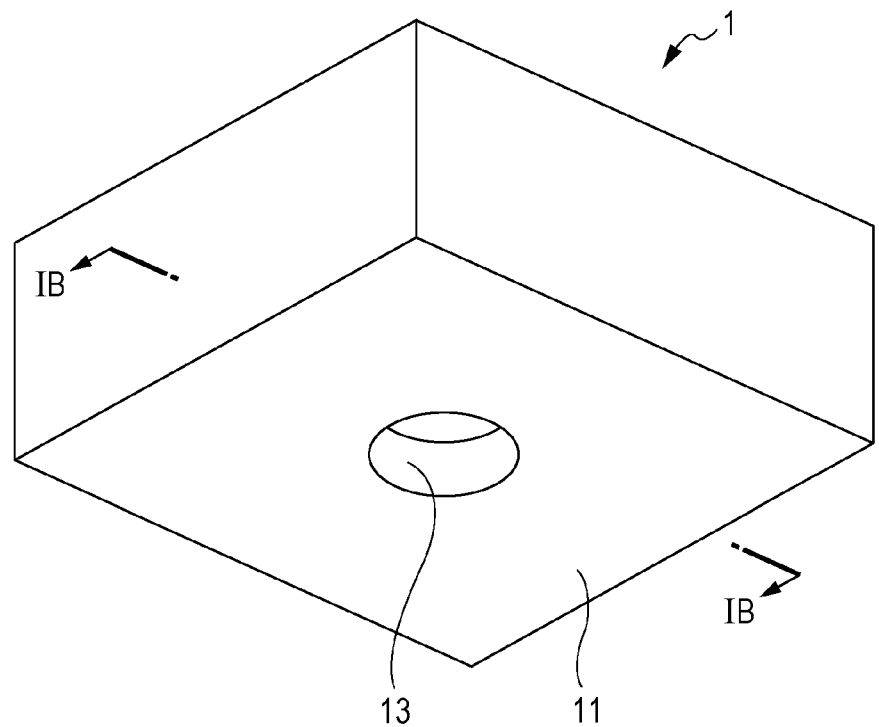
FIG. 1A is a schematic diagram illustrating an entire configuration of a measurement device according to a first embodiment.
Figure 1B:
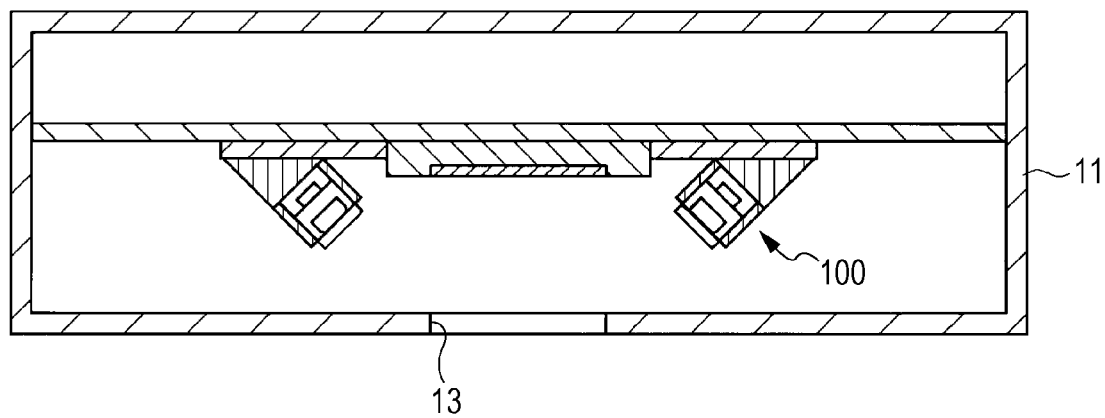
FIG. 1B is a schematic diagram illustrating an entire configuration of the measurement device according to the same embodiment.

1. First Embodiment 1-1. Entire Configuration of Measurement Device
1-2. Configuration of Optical System 2. Second Embodiment 2-1. Configuration of Optical System 3. Application Examples of Measurement Device First Embodiment Entire Configuration of Measurement Device First, with reference to FIGS. 1A and 1B, an entire configuration of a measurement device according to a first embodiment will be described briefly. FIGS. 1A and 1B are schematic diagrams illustrating an entire configuration of a measurement device according to the embodiment.

The measurement device 1 according to the embodiment has a casing 11 made of an arbitrary substance as shown in FIG. 1A, and an opening portion 13 is provided at a part of the casing 11. In FIG. 1A, the shape of the opening portion 13 is a circular shape, and the shape of the opening portion 13 is not limited to the circular shape but may be a polygonal shape or an oval shape. A measurement target (for example, a human skin surface or the like) is placed on the part of the opening portion 13, and the measurement device 1 according to the embodiment measures the placed measurement target. In addition, the opening portion 13 has the size of the throughhole; however, it may be appropriately determined according to the size of a light sensing element included in an optical system 100 described later.

FIG. 1B is a cross-sectional view taken along the line IB-IB in FIG. 1A.

As shown in FIG. 1B, the inside of the casing 11 is hollow, and an optical system 100 of the measurement device 1 according to the embodiment is installed inside the casing 11. In addition, the inner walls of the casing 11 are preferably black or a color tone similar to black in order to suppress reflection of leakage light from the optical system 100.

Here, the optical system 100 installed inside the casing 11 will be described again in detail. In FIG. 1B, although only the optical system 100 is shown to be present inside the casing 11, arbitrary units may be installed inside the casing 11 in addition to the optical system 100 in a range not having influence on the measurement process in the optical system 100.

Configuration of Optical System

Figure 2:
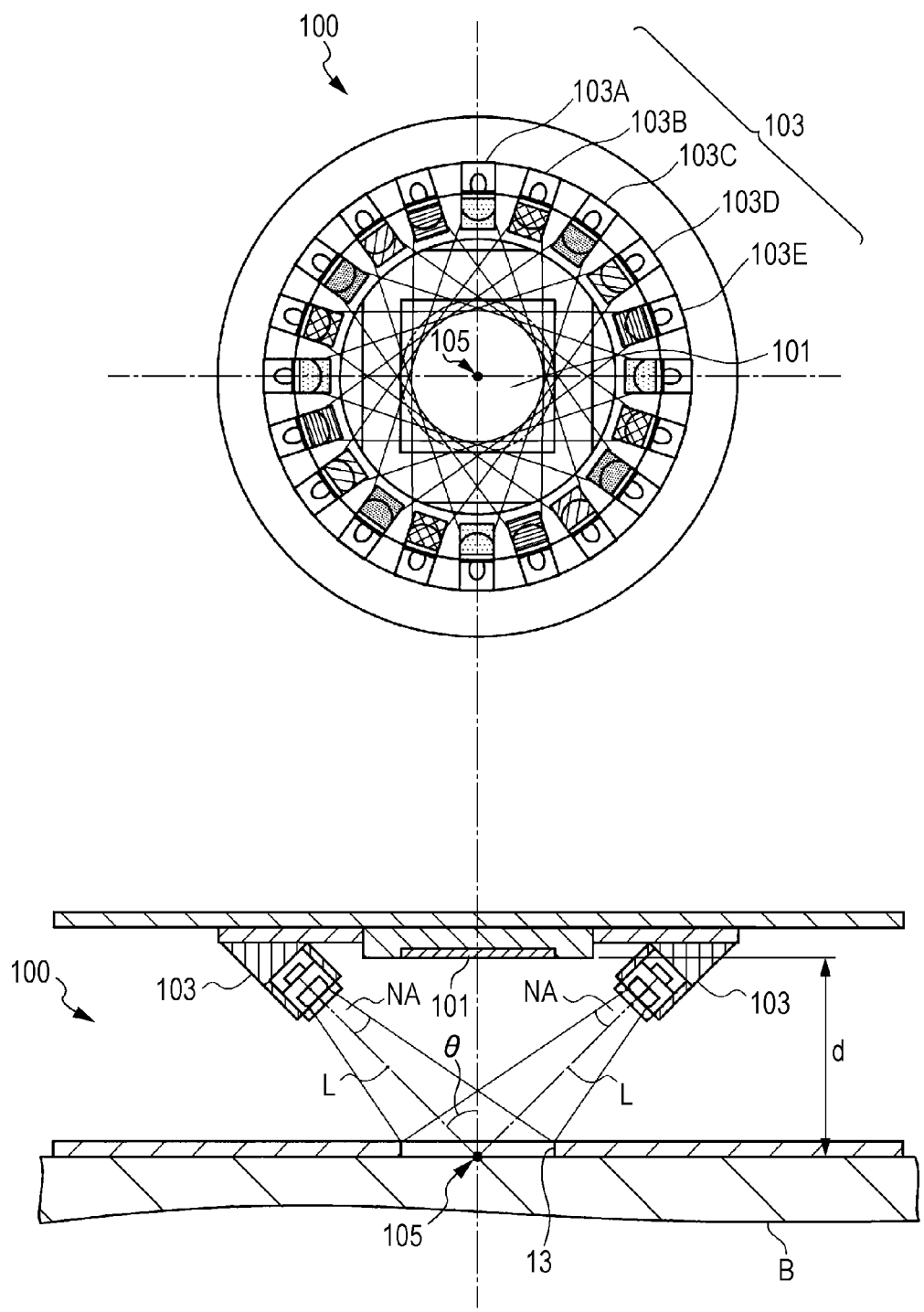
FIG. 2 is a diagram illustrating an example of an optical system included in the measurement device according to the same embodiment.

Next, referring to FIG. 2, the optical system included in the measurement device 1 according to the embodiment will be described in detail. FIG. 2 is a diagram illustrating an example of the optical system included in the measurement device according to the embodiment.

The upper part of FIG. 2 is a plan view when the optical system 100 according to the embodiment is viewed from the side of the opening portion 13, and the lower part of FIG. 2 is a cross-sectional view when the optical system 100 according to the embodiment is taken along the central line of the upper part of FIG. 2. In addition, in the example shown in FIG. 2, a case will be described in which a human skin surface B is placed on the opening portion 13, and the skin surface B placed on the opening portion 13 is a measurement target region.

As shown in FIG. 2, the optical system 100 according to the embodiment has a light sensing element 101 which is disposed at a containing unit having an arbitrary shape such as a substrate, and a plurality of light emitting elements 103 which are disposed at a containing unit having an arbitrary shape such as a substrate.

Light (reflection light) from the measurement target region on which the measurement target is placed forms an image on the light sensing element 101. The light sensing element 101 generates data or the like indicating the light amount of the light forming an image according to the light amount of the light forming an image on a light sensing surface. An example of the light sensing element 101 includes a photodiode; however, the light sensing element 101 according to the embodiment is not limited thereto, and may use other optical sensors. In addition, the light sensing element 101 may measure other physical quantities such as a luminance value of light forming an image instead of the light amount of the light forming an image on the light sensing surface.

The light sensing element 101 is disposed to face the opening portion 13 provided at the casing 11 of the measurement device 1 as shown in FIG. 2. In other words, the light sensing element 101 is disposed to face substantially in parallel to the opening portion 13. In addition, the size of the light sensing element 101 may be appropriately determined according to the through-hole provided as the opening portion 13, and, for example, may use a small-sized optical sensor of 10 mm×10 mm or the like. In a case of using the small-sized optical sensor, the size of the opening portion 13 is preferably, 10 mm ϕ.

As shown in the upper part of FIG. 2, a plurality of light emitting elements 103 are disposed around the light sensing element 101 in a ring shape. As the light emitting elements 103, for example, a light emitting diode may be used.

The light emitting elements 103 are disposed uniformly at the same interval with respect to the center 105 of the opening portion 13. For example, 4N (where N is an integer equal to or more than 1) light emitting elements 103 are disposed at an interval of (90/N)° with respect to the center 105 of the opening portion 13. The number of the light emitting elements 103 disposed around the light sensing element 101 may be appropriately set according to the size of the light sensing element 101, the size of the measurement device 1 itself, or the like; however, for example, twenty light emitting elements 103 are preferably disposed at an interval of 18°.

In addition, a wavelength of light radiated by the light emitting elements 103 may be appropriately selected depending on what kind of features are measured from a measurement target; however, for example, light emitting elements capable of radiating light of visible light band (about 400 nm to 700 nm) are preferably used.

The plurality of light emitting elements 103, as shown in the lower part of FIG. 2, are disposed to be tilted with respect to the normal line of the measurement target region such that the central line L of emission radiated from each of the light emitting elements 103 passes through the center 105 of the measurement target region. In addition, the size of a spot formed in the measurement target region by the emission radiated from each of the light emitting elements 103 is preferably substantially the same (almost overlap each other) as the size of the opening portion 13, as shown in the lower part of FIG. 2. In the lower part of FIG. 2, an angle formed by the central line L of the radiated emission and the normal line of the measurement target region is denoted by θ. Hereinafter, the angle θ is referred to as an installation angle of the light emitting elements 103.

The installation angle of the light emitting elements 103 is set according to a separation distance (the distance d in the lower part of FIG. 2) between the measurement target region and the light sensing element 101. That is to say, if the separation distance d is equal to or less than a predetermined threshold value (for example, 20 mm), the installation angle θ is set to 45°, and if the separation distance is larger than a predetermined threshold value (for example, 20 mm), the installation angle θ may be set to below 45° (preferably, 20° to 30°).

If the miniaturization of the measurement device is not oriented, the separation distance between the measurement target region and the light sensing element 101 may be set to any large value; however, in the measurement device 1 according to the embodiment, the upper limit of the separation distance d is preferably about 40 mm.

Figure 3:
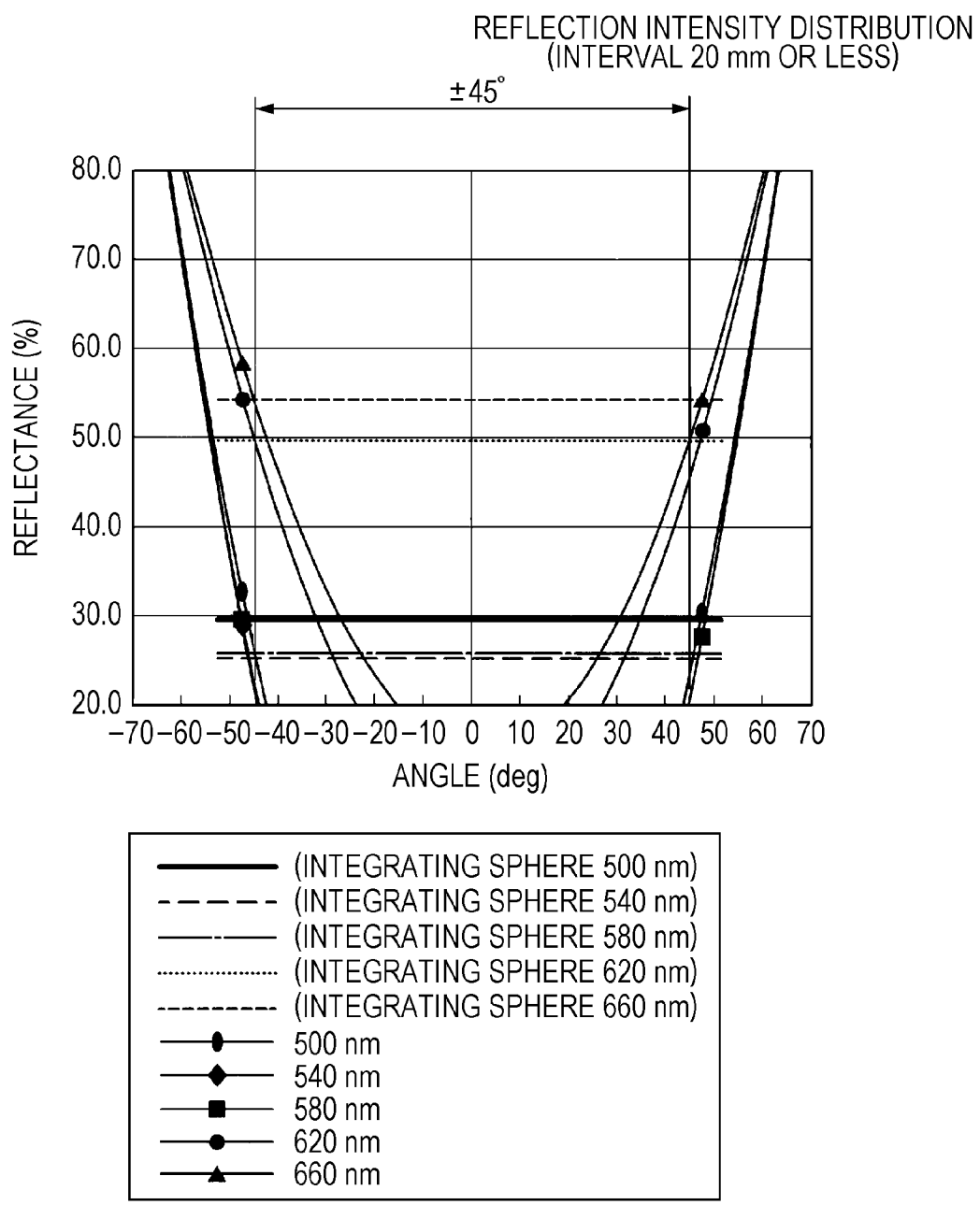
FIG. 3 is a graph diagram illustrating a relationship between an installation angle and a reflection light amount detected by a light sensing element.
Figure 4:
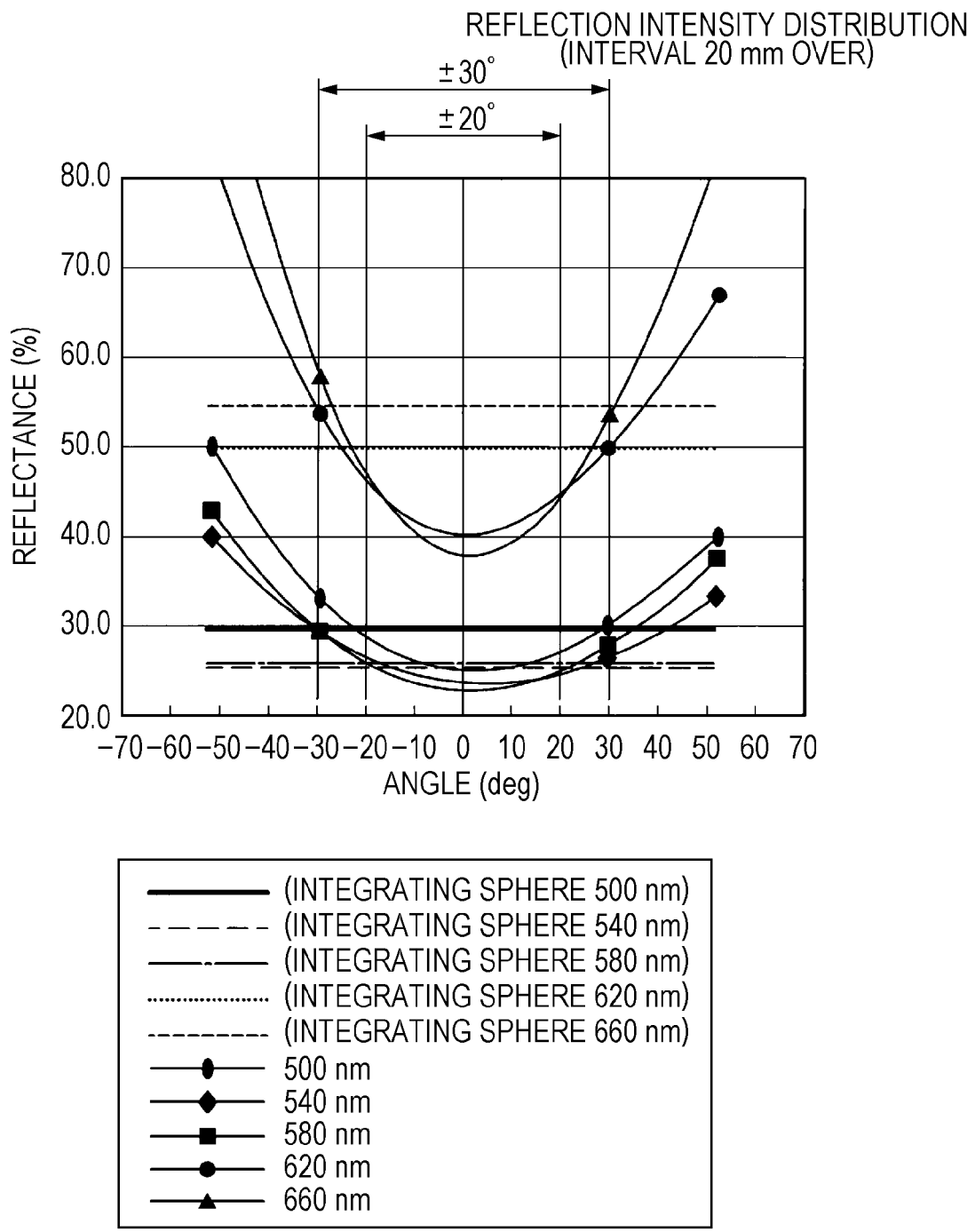
FIG. 4 is a graph diagram illustrating a relationship between an installation angle and a reflection light amount detected by a light sensing element.

Here, the relationship between the installation angle θ of the light emitting elements 103 and the separation distance d will be described in detail with reference to FIGS. 3 and 4. FIGS. 3 and 4 are graph diagrams illustrating the relationship between the installation angle θ and the reflection light amount detected by the light sensing element.

First, FIG. 3 is referred to. FIG. 3 shows a result where a white diffuse reflection plate is disposed at the opening portion 13, and the light sensing element 101 measures the reflection light amount when light radiated from the light emitting elements 103 is reflected, in a case where the separation distance d between the measurement target region and the light sensing element 101 in the measurement device shown in FIG. 2 is 20 mm. In addition, in FIG. 3, the transverse axis expresses the installation angle θ of the light emitting elements, and the longitudinal axis expresses the reflectance (%) with respect to the light amount 100% reflected by the white diffuse reflection plate.

Here, wavelengths of the light radiated from the light emitting elements 103 are set to five kinds, 500 nm, 540 nm, 580 nm, 620 nm, and 660 nm, and the reflectance of each wavelength is measured.

In addition, the graph diagram shown in FIG. 3 shows the reflectance for the five wavelengths practically measured using the integrating sphere used in a spectrometry device in the related art together.

The integrating sphere integrates and averages an angle component by collecting light from multiple angles, and thus the reflectance measured does not depend on an angle, and the measured result shows a horizontal line, as shown in FIG. 3. On the other hand, if the installation angle θ is varied and the reflectance is measured in the optical system 100 shown in FIG. 2, a result thereof is indicated by the solid lines in FIG. 3. As is clear from FIG. 3, in the result of measuring the reflectance while varying the installation angle θ, the values of the reflectance measured are varied according to the installation angle θ, and thus it can be seen that the measured reflectance has the angle dependency.

In FIG. 3, an intersection point between the result of performing the measurement while varying the installation angle θ and the reflectance using the integrating sphere has an important meaning. In other words, the installation angle θ corresponding to the intersection point is an installation angle of the light emitting elements which can correctly perform the measurement without using the integrating sphere.

In a case of FIG. 3, when attention is paid to the wavelengths of 500 nm, 540 nm, 580 nm, 620 nm, and 660 nm in the visible light band (400 nm to 700 nm), it can be seen that the intersection points between the result measured using the integrating sphere and the result which is practically measured in the optical system 100 according to the embodiment are in a range of ±45°. Therefore, if the separation distance d is 20 mm in the optical system 100 according to the embodiment, the installation angle θ is preferably 45°.

Further, in the example shown in FIG. 3, although the measurement result is shown in a case where the separation distance d is 20 mm, the measurement result of reflectance shows the same result as in FIG. 3 in a range of the separation distance d≤120 mm even in examples other than 20 mm. Therefore, in the optical system 100 according to the embodiment, in a case where the separation distance d is within 20 mm, the installation angle θ of the light emitting elements 103 is preferably 45°.

Next, FIG. 4 is referred to. FIG. 4 shows a result where a white diffuse reflection plate is disposed at the opening portion 13, and the light sensing element 101 measures the reflection light amount when light radiated from the light emitting elements 103 is reflected, in a case where the separation distance d between the measurement target region and the light sensing element 101 in the measurement device shown in FIG. 2 is 21 mm. In addition, in FIG. 4 as well, the transverse axis expresses the installation angle θ of the light emitting elements, and the longitudinal axis expresses the reflectance (%) with respect to the light amount 100% reflected by the white diffuse reflection plate.

As is clear from FIG. 4, if the separation distance d exceeds 20 mm, it can be seen that the angle dependency of the reflectance of the optical system 100 according to the embodiment is varied as compared with the case where the separation distance d is equal to or less than 20 mm. As a result, the intersection points with the result measured using the integrating sphere are located at positions lower than ±45° in the case of the separation distance d≤20 mm. Therefore, if the separation distance d exceeds 20 mm, the installation angle θ of the light emitting elements 103 is preferably less than 45°. In addition, in FIG. 4, it can be seen that the installation angle θ is preferably ±20° to ±30° in the noted five wavelengths.

As such, in the optical system 100 according to the embodiment, the installation angle θ of the light emitting elements 103 is determined based on the reflectance at each wavelength in a case of being measured using the integrating sphere. Thereby, in the optical system 100 according to the embodiment, it is possible to more accurately measure light reflected from the measurement target region.

Referring to FIG. 2 again, the light emitting elements 103 according to the embodiment will be described.

It is preferable that the light emitting elements 103 according to the embodiment can radiate light of low numerical aperture. The light of low numerical aperture may be realized by light emission itself of the light emitting element 103, or may be realized by combining a predetermined condensing lens with the light emitting elements. Here, the numerical aperture of the radiated emission from the light emitting element 103 is set such that the curve indicating the installation angle dependency of the reflectance in FIGS. 3 and 4 intersects the measurement result of the reflectance measured using the integrating sphere.

Figure 5:
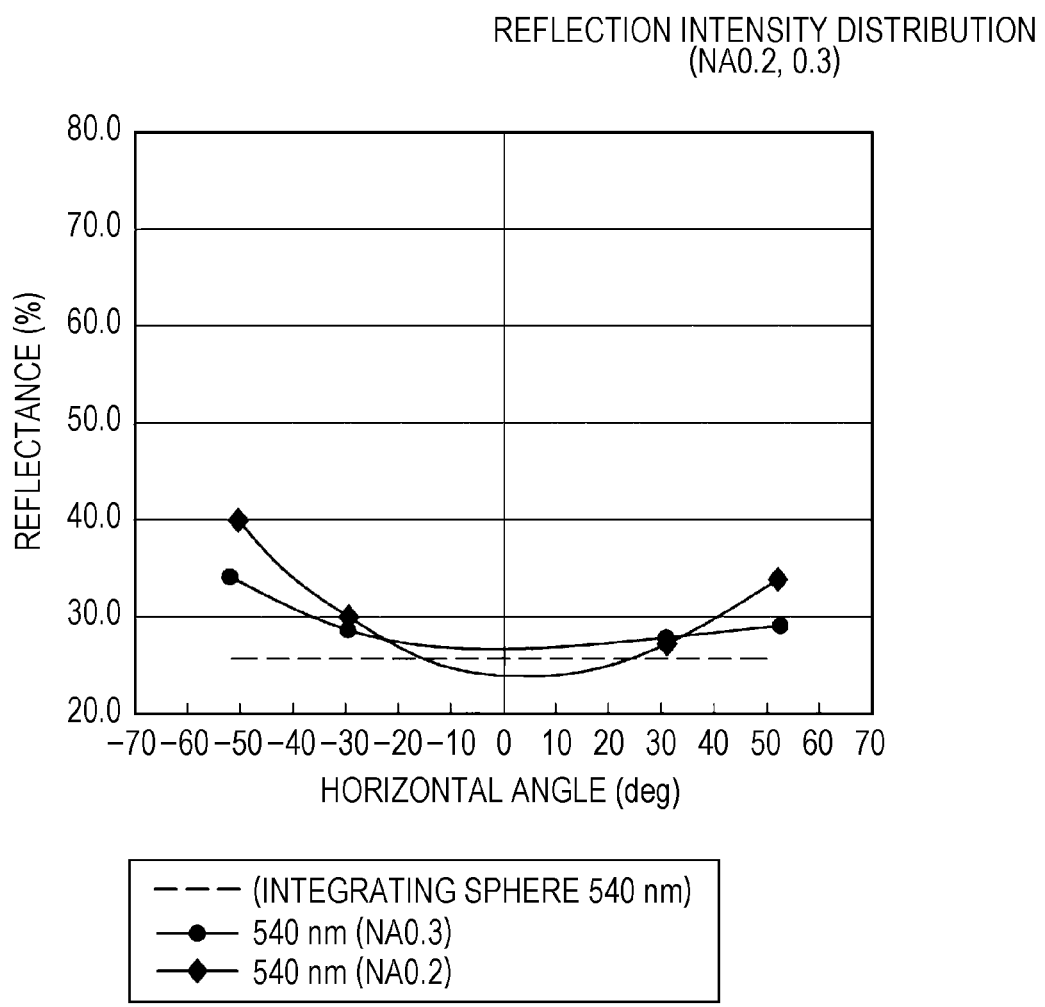
FIG. 5 is a graph diagram illustrating a relationship between a numerical aperture of a light emitting element and reflectance.

The installation angle dependency of the reflectance shown in FIGS. 3 and 4 is a result measured using the light emitting elements 103 having the numerical aperture NA=0.2. In addition, the graph diagram shown in FIG. 5 shows a measurement result of the reflectance in a case where the numerical aperture of the light emitting element is set to 0.2 and 0.3 when paying attention to light of the wavelength 540 nm. As is clear from FIG. 5, if the separation distance is set to a large value equal to or more than a predetermined threshold value, the curve indicating the installation angle dependency of the reflectance does not intersect the measurement result of the reflectance measured using the integrating sphere. Therefore, the numerical aperture of the radiated emission of the light emitting element 103 is set such that the curve indicating the installation angle dependency of the reflectance intersects the measurement result of the reflectance measured using the integrating sphere. In the examples shown in FIGS. 3 to 5, the numerical aperture NA of the radiated emission is set to be 0.2 or less, thereby the curve indicating the installation angle dependency of the reflectance intersects the measurement result of the reflectance measured using the integrating sphere, and thus an appropriate installation angle θ can be determined.

Referring to FIG. 2 again, the light emitting elements 103 according to the embodiment will be further described.

The optical system 100 according to the embodiment, as described above, has 4N (where N is an integer equal to or more than 1) light emitting elements 103 at an interval of (90/N)°, and, in the example shown in the upper part of FIG. 2, the optical system 100 has twenty light emitting elements 103 at an interval of 18°.

Here, in the optical system 100 according to the embodiment, the light emitting elements which can radiate light of different N wavelengths are provided by four for each wavelength. For example, in the example in the upper part of FIG. 2, the light emitting elements 103A to 103E which can respectively radiate light of five wavelengths are provided by four for each wavelength. In this case, the light emitting elements 103 radiating light of the same wavelength are disposed around the light sensing element 101, for example, at an interval of 90°. Thereby, the light emitting elements 103 radiating light of the same wavelength are disposed to lie in the point symmetry with respect to the center 105 of the opening portion 13.

Here, the light of N wavelengths may be provided by the light emitting elements singly, or may be provided by a combination of an optical filter transmitting light of a predetermined wavelength therethrough and the light emitting elements (for example, a combination of an optical filter and white light emitting elements).

In addition, the kind of wavelengths of light radiated by a plurality of light emitting elements 103 may be determined according to a phenomenon or a substance which is a measurement target, or a wavelength which enables a phenomenon or a substance, which is a measurement target, to be measured with good efficiency may be appropriately selected (in other words, a wavelength distinctive to the phenomenon or the substance which is a measurement target). For example, if human skin is a measurement target, as described below, it is preferable to select five kinds of light having wavelengths of 500 nm, 540 nm, 580 nm, 620 nm, and 660 nm as central wavelengths.

Figure 6:
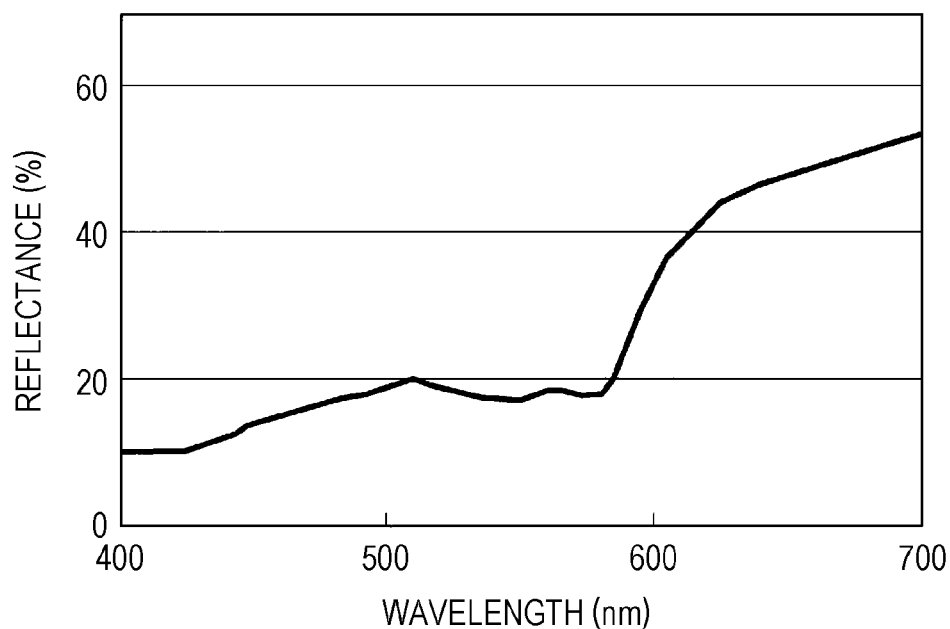
FIG. 6 is a graph diagram illustrating the wavelength characteristic of reflectance of skin.

FIG. 6 shows a result of measuring the reflectance of human skin at the visible light wavelength band (400 nm to 700 nm). As is clear from FIG. 6, the reflectance of the human skin smoothly increases at the band of around 400 nm to 500 nm, the reflectance slightly decreases up to the band of around 600 nm, and then the reflectance rapidly increases from the band of around 600 nm up to the band of around 650 nm.

Here, in a case where the human skin is a measurement target, the reason why attention is paid to the overall visible light wavelength band as shown in FIG. 6 is that a light source capable of radiating all the types of light of the visible light wavelength band is necessary, and a spectral element such as a diffraction grating is necessary in order to specify the light amount for each wavelength. As a result, it is predicted that the measurement device will be difficult to miniaturize.

Therefore, in the measurement device 1 according to the embodiment, by selecting N wavelengths distinctive to a phenomenon or a substance which is a measurement target, the phenomenon or the substance which is a measurement target is measured with good efficiency without using a special light source or a spectral element. For example, in a case of the human skin shown in FIG. 6, wavelength positions distinctive to the spectrum are five points shown in FIG. 7. Therefore, in the measurement device 1 according to the embodiment, the human skin is measured with good efficiency by paying attention to the five wavelengths shown in FIG. 7. In addition, the five wavelengths are useful to a case where various kinds of hemoglobin such as an oxygenated hemoglobin, glycosylated hemoglobin, and reduced hemoglobin, which are present in human blood which is a measurement target.

In addition, in a case where the measurement device 1 may not mount all the light emitting elements 103 which can provide light of wavelengths distinctive to a phenomenon or a substance which is a measurement target thereon, some of the distinctive wavelengths may be selected according to the number of light emitting elements which can be mounted. For example, in a case where the light emitting elements of 5×4=20 may not be mounted when the human skin is a measurement target, the wavelengths may be selected one by one from a distinctive wavelength among the five wavelengths. In the spectrum shown in FIG. 6, the most distinctive wavelength is the wavelength of 580 nm corresponding to a position where the reflectance rapidly increases. Therefore, for example, in a case where only three wavelengths are selected, first, the wavelength of 580 nm is selected, then one wavelength of 500 nm and 540 nm may be selected, and thereafter one wavelength of 620 nm and 660 nm may be selected.

Here, in a case where the human skin is a measurement target and attention is paid to the five wavelengths, the full width at half maximum of light having 580 nm as a central wavelength is preferably smaller than the full width at half maximum of light having 500 nm, 540 nm, 620 nm, and 660 nm as a central wavelength. Specifically, it is preferable that the full width at half maximum of the light having 580 nm as a central wavelength be 10 nm to 20 nm, and the full width at half maximum of the light having 500 nm, 540 nm, 620 nm, and 660 nm as a central wavelength be 30 nm to 50 nm. The reason therefor will be described in detail with reference to FIGS. 6 and 8.

As shown in FIG. 6, the reflectance of the human skin rapidly increases around the wavelength 580 nm, and the variations in the reflectance in other wavelength bands are relatively smooth. Thus, in order to accurately measure the reflectance at the central wavelength 580 nm, the wavelength width of the central wavelength is preferably narrower than other central wavelengths.

Figure 8:
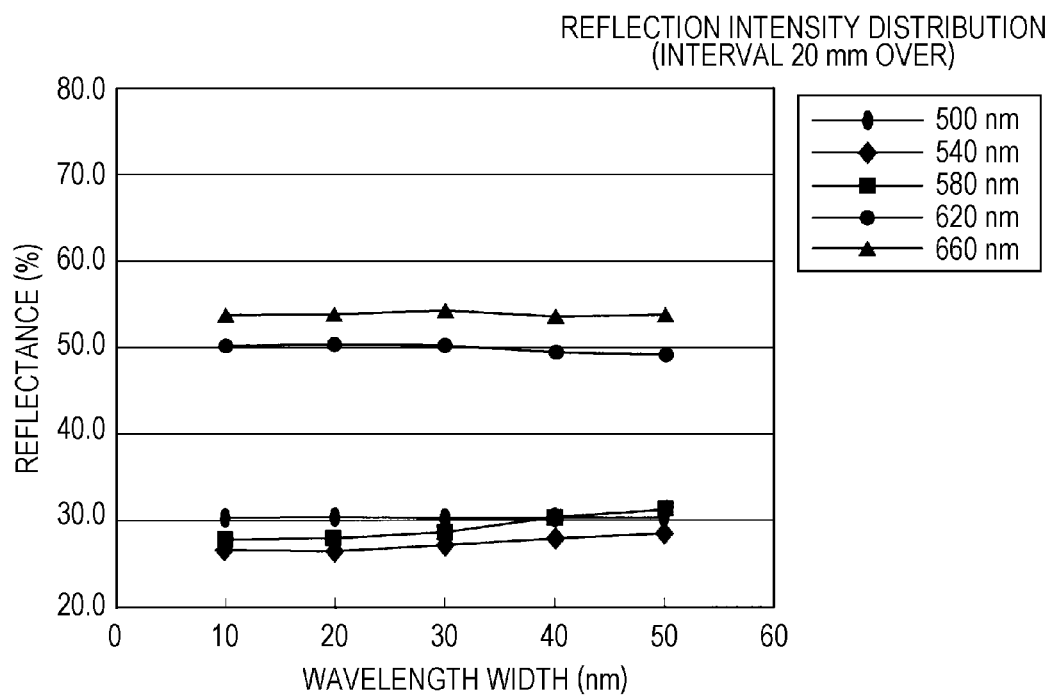
FIG. 8 is a graph diagram illustrating a relationship between the full width at half maximum of a central wavelength and reflectance.

FIG. 8 is a graph diagram illustrating a relationship between the full width at half maximum of the central wavelength and the observed reflectance. The graph diagram is created by measuring the reflectance observed when the irradiation is performed while varying the full width at half maximum of light having 500 nm, 540 nm, 580 nm, 620 nm, and 660 nm as a central wavelength. From FIG. 8, it can be seen that the light of the central wavelength 580 nm tends to increase the reflectance if the full width at half maximum is equal to or more than 20 nm. On the other hand, it can be seen that light of the other wavelengths has no difference in the reflectance if the full width at half maximum is equal to or less than 30 nm, and the reflectance does not greatly vary even if the full width at half maximum is equal to or less than 50 nm. From this result, as described above, it can be seen that it is preferable that the full width at half maximum of the light of the central wavelength 580 nm be 10 nm to 20 nm, and the full width at half maximum of the light of the central wavelengths 500 nm, 540 nm, 620 nm, and 660 nm be 30 nm to 50 nm.

Figure 9:
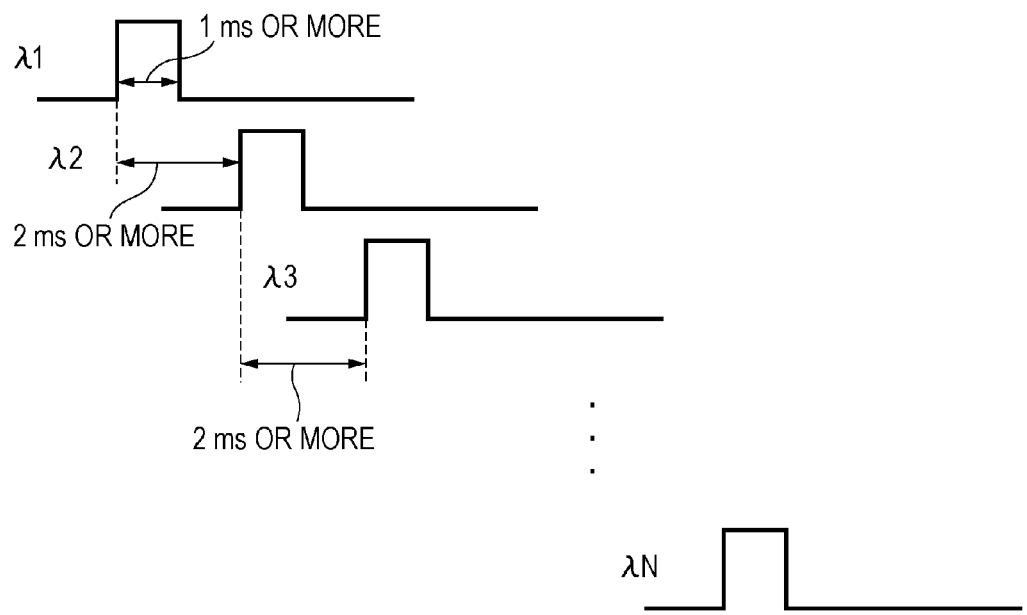
FIG. 9 is a diagram illustrating an example of a light emitting timing of the light emitting element according to the same embodiment.

As described above, in the optical system 100 of the measurement device 1 according to the embodiment, the 4N light emitting elements 103 radiates light of N wavelengths to the measurement target region; however, it is preferable that irradiation timings of N wavelengths be delayed and the measurement target region be irradiated with the light. For example, as shown in FIG. 9, in a case where the light emitting elements 103 radiate light of a predetermined wavelength when one pulse waveform is input to the light emitting elements 103, the light of the N wavelengths is preferably emitted using N pulse waveforms in a time divisional manner. At this time, in order to secure the light amount enough to perform the measurement with one irradiation, the width of the pulse waveform is preferably, for example, equal to or more than 1 ms at each wavelength $\lambda N$. In addition, in order to prevent light of different wavelengths from being mixed, a temporal position of a pulse waveform regarding the t-th wavelength $\lambda t$ and a temporal position of a pulse waveform regarding the (t+1)-th wavelength $\lambda t+1$ are preferably, for example, equal to or more than 2 ms.

As described above, through the control of light emission in a time divisional manner, the light of N wavelengths are sequentially provided to the measurement target region, and reflection light corresponding to each wavelength forms an image on the light sensing element 101. As a result, the light sensing element 101 can accurately measure the light amount of the reflection light corresponding to each wavelength.

As such, as described above with reference to FIGS. 2 to 9, in the measurement device 1 according to the embodiment, the measurement target region is sequentially irradiated with the light of N wavelengths, and the light sensing element measures reflection light corresponding to each wavelength, thereby obtaining optical information for the measurement target placed on the measurement target region. Further, since the measurement is performed after the wavelengths distinctive to a phenomenon or a substance which is a measurement target are selected in advance, in the measurement device 1 according to the embodiment, an optical unit such as the integrating sphere or the diffraction grating is not necessary, and thereby the minimization of the device can be realized. Since the photodiode can be used as a light source of light of N wavelengths, it is possible to realize electric power conservation and a cost reduction even in a case where 4N light emitting elements are mounted.

Second Embodiment

The measurement device 1 according to the first embodiment irradiates the measurement target region with the light of N wavelengths at different timings, and measures the measurement target placed on the measurement target region. In the measurement device 1 according to the second embodiment described below, 4N light emitting elements irradiate the measurement target region with light having the same wavelength at the same time, and measure the measurement target placed on the measurement target region. At this time, in the measurement device 1 according to the second embodiment, an optical filter is disposed right before the light sensing element 101, and N wavelengths of interest are selected.

Configuration of Optical System

Figure 10:
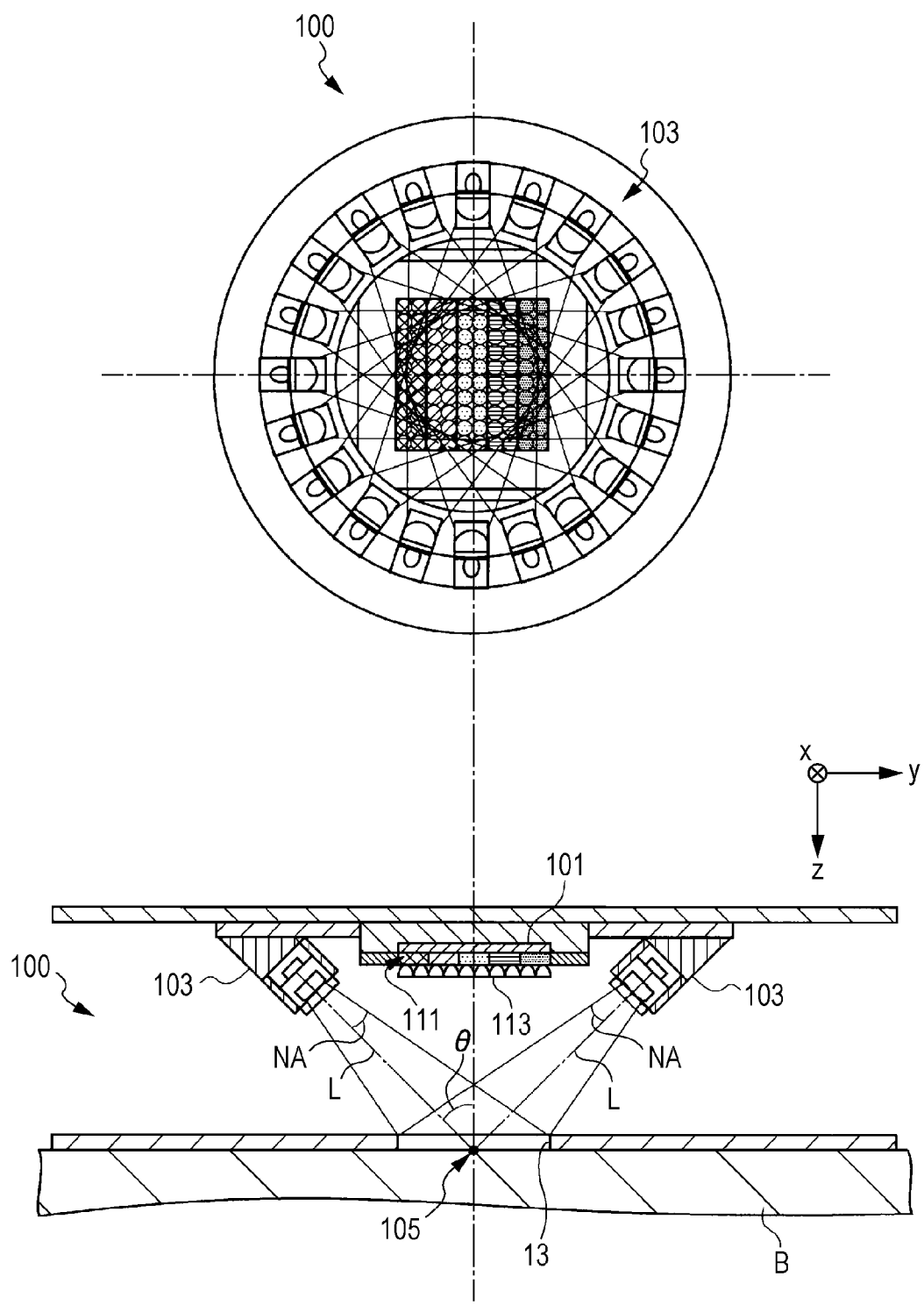
FIG. 10 is a diagram illustrating an example of an optical system included in a measurement device according to a second embodiment.

An exterior appearance of the measurement device 1 according to the embodiment is the same as the exterior appearance of the measurement device 1 according to the first embodiment shown in FIG. 1A, and thus detailed description thereof will be omitted. Hereinafter, with reference to FIG. 10, a configuration of the optical system 100 included in the measurement device 1 according to the embodiment will be described in detail. FIG. 10 is a diagram illustrating an example of the optical system included in the measurement device according to the embodiment.

The upper part of FIG. 10 is a plan view when the optical system 100 according to the embodiment is viewed from the side of the opening portion 13, and the lower part of FIG. 10 is a cross-sectional view when the optical system 100 according to the embodiment is taken along the central line of the upper part of FIG. 10. In addition, in the example shown in FIG. 10, a case will be described in which a human skin surface B is placed on the opening portion 13, and the skin surface B placed on the opening portion 13 is a measurement target region.

As shown in FIG. 10, the optical system 100 according to the embodiment has a light sensing element 101 which is disposed at a containing unit having an arbitrary shape such as a substrate, and a plurality of light emitting elements 103 which are disposed at a containing unit having an arbitrary shape such as a substrate. In addition, an optical filter 111 and a collimate lens 113 are provided at the upper side (z axis positive direction in the lower part of FIG. 10) of the light sensing surface of the light sensing element 101.

Within reflection light from the measurement target placed on the measurement target region, light passing through the collimate lens 113 and the optical filter 111 forms an image on the light sensing element 101. The light sensing element 101 generates data or the like indicating the light amount of the light forming an image according to the light amount of the light forming an image on a light sensing surface. An example of the light sensing element 101 includes a photodiode; however, the light sensing element 101 according to the embodiment is not limited thereto, but may use other optical sensors.

The light sensing element 101 is disposed to face the opening portion 13 provided at the casing 11 of the measurement device 1 in a manner similar to the first embodiment.

As shown in the upper part of FIG. 10, a plurality of light emitting elements 103 having the same emission characteristic as each other are disposed around the light sensing element 101 in a ring shape. As the light emitting elements 103, for example, a light emitting diode may be used in a manner similar to the first embodiment.

The light emitting elements 103 are disposed uniformly at the same interval with respect to the center 105 of the opening portion 13. For example, 4N (where N is an integer equal to or more than 1) light emitting elements 103 are disposed at an interval of (90/N)° with respect to the center 105 of the opening portion 13. The number of light emitting elements 103 disposed around the light sensing element 101 may be appropriately set according to the size of the light sensing element 101, the size of the measurement device 1 itself, or the like; however, for example, twenty light emitting elements 103 are preferably disposed at an interval of 18°.

In addition, a wavelength of light radiated by the light emitting elements 103 may be appropriately selected depending on what kind of features are measured from a measurement target; however, for example, light emitting elements 103 capable of radiating light of a wavelength band including all wavelengths distinctive to the measurement target are preferably used. It is possible to measure that the wavelengths distinctive to the measurement target are present in the visible light band (about 400 nm to 700 nm) by using, for example, white light emitting elements as the light emitting elements 103 according to the embodiment.

The plurality of light emitting elements 103, as shown in the lower part of FIG. 10, are disposed to be tilted with respect to the normal line of the measurement target region such that the central line L of emission radiated from each of the light emitting elements 103 passes through the center 105 of the measurement target region. In addition, the size of a spot formed by the emission radiated from each of the light emitting elements 103 is preferably substantially the same (almost overlap each other) as the size of the opening portion 13, as shown in the lower part of FIG. 10.

The installation angle θ and the numerical aperture NA of the light emitting element 103 may be determined according to the reference described in the first embodiment, and are preferably be a numerical range similar to the first embodiment.

Figure 11:
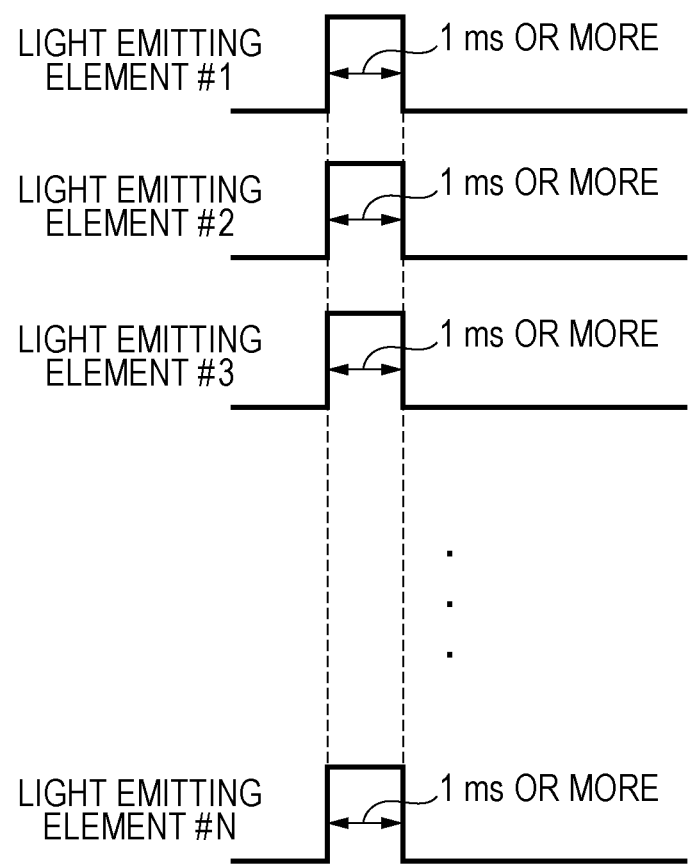
FIG. 11 is a diagram illustrating an example of a light emitting timing of the light emitting element according to the same embodiment.

It is preferable that the plurality of light emitting elements 103 radiate light having the same wavelength characteristic as described above, and the plurality of light emitting elements 103 emit light at the same time. For this reason, for example, as shown in FIG. 11, in a case where the light emitting elements 103 radiate white light when one pulse waveform is input to the light emitting elements 103, N pulse waveforms are simultaneously input to the plurality of light emitting elements 103, and thereby the plurality of light emitting elements 103 emit light at the same time. At this time, in order to secure the light amount enough to perform the measurement with one irradiation, the width of the pulse waveform is preferably, for example, equal to or more than 1 ms.

Here, in the measurement device 1 according to the embodiment as well, the measurement is performed by paying attention to wavelengths distinctive to the measurement target, and, in the following description, it is assumed that N distinctive wavelengths are present in the measurement target (for example, a human skin surface). In this case, the optical system 100 of the measurement device 1 according to the embodiment measures the light amount or the like for the N distinctive wavelengths by using reflection light where light having the same wavelength characteristic (for example, white light emission) emitted from the light emitting elements 103 is reflected by the measurement target surface.

In the optical system 100 according to the embodiment, the optical filter 111 is used as shown in the lower part of FIG. 10, in order to select light of a wavelength of interest from the reflection light using the white light source. The optical filter 111 is provided at the upper side the light sensing surface of the light sensing element 101 so as to correspond to the number of the wavelengths of interest. In the embodiment, attention is paid to N distinctive wavelengths, and thus N optical filters 111 are used.

The optical filter 111 is an optical element (for example, a bandpass filter) which transmits light of a specific wavelength band therethrough as described above. In the optical system 100 according to the embodiment, the optical filter 111 may be appropriately selected according to wavelength bands to which attention is paid as the wavelengths distinctive to the measurement target. In the embodiment, since attention is paid to N wavelengths, N optical filters 111 which individually transmit each of N wavelengths therethrough are selected.

Here, for each optical filter 111, a wavelength bandwidth of light which passes through the filter may be appropriately set according to a characteristic of a wavelength to which attention is paid.

The reflection light which has passed through the optical filters 111 forms an image on a specific region of the light sensing element 101. Therefore, the measurement device 1 according to the embodiment grasps positional relationships between the light sensing element 101 and the respective plurality of optical filters 111, and can thereby specify that the light forming an image on a certain region of the light sensing element 101 is light corresponding to which wavelength band.

In addition, in order to make the reflection light (diffuse reflection light) from the measurement target surface efficiently incident to the optical filters 111, the collimate lens 113 such as a rod lens may be disposed upstream the optical filter 111 (z axis positive direction side in the lower part of FIG. 10). The diffuse reflection light incident to the collimate lens 113 is changed to parallel light beams by the collimate lens 113, and then is incident to the optical filters 111.

Next, in a manner similar to the first embodiment, for example, in a case where the human skin surface is a measurement target, the optical system 100 according to the embodiment, particularly, the light sensing element 101 and the optical filters 111 will be described in detail.

Figure 7:
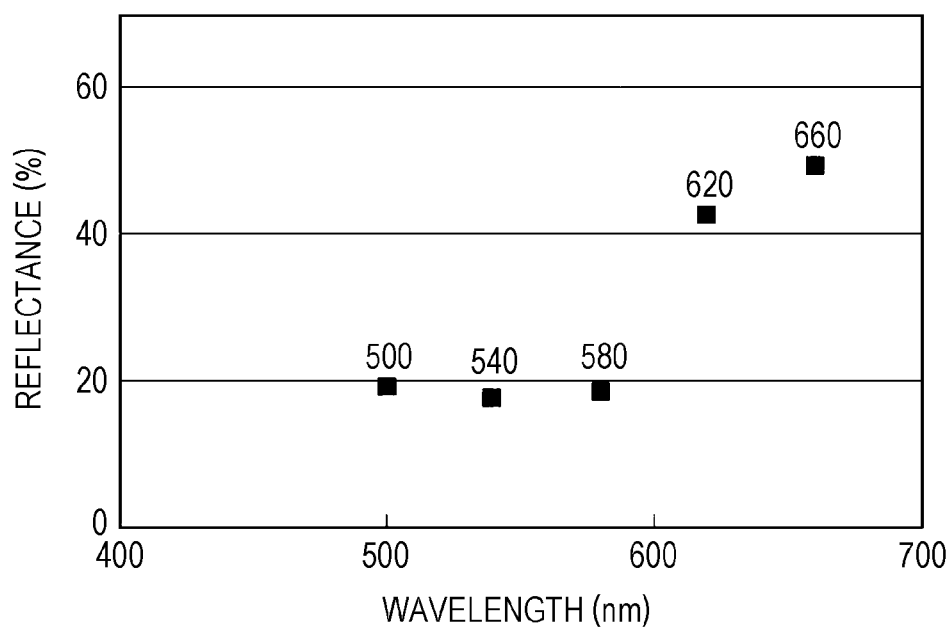
FIG. 7 is a graph diagram illustrating the wavelength characteristic of reflectance of skin.

As described with reference to FIGS. 6 and 7, the wavelengths distinctive by the reflection light from the human skin surface are five kinds of 500 nm, 540 nm, 580 nm, 620 nm, and 660 nm. Therefore, in order to measure the light amount or the like of the light of five wavelengths, as shown in the upper part of FIG. 12, the light sensing element 101 may be divided into five regions 101A to 101E. In the light sensing element 101, the five regions may be divided physically or virtually (for convenience of a process). Among the five regions of the light sensing element 101, for example, the region 101A is a region on which light of the wavelength A forms an image, and the region 101B is a region on which light of the wavelength B forms an image. Here, in a case of using a photodiode having the size of 10 mm×10 mm as the light sensing element 101, the photodiode may be divided into five regions every 2×10 mm.

Figure 12:
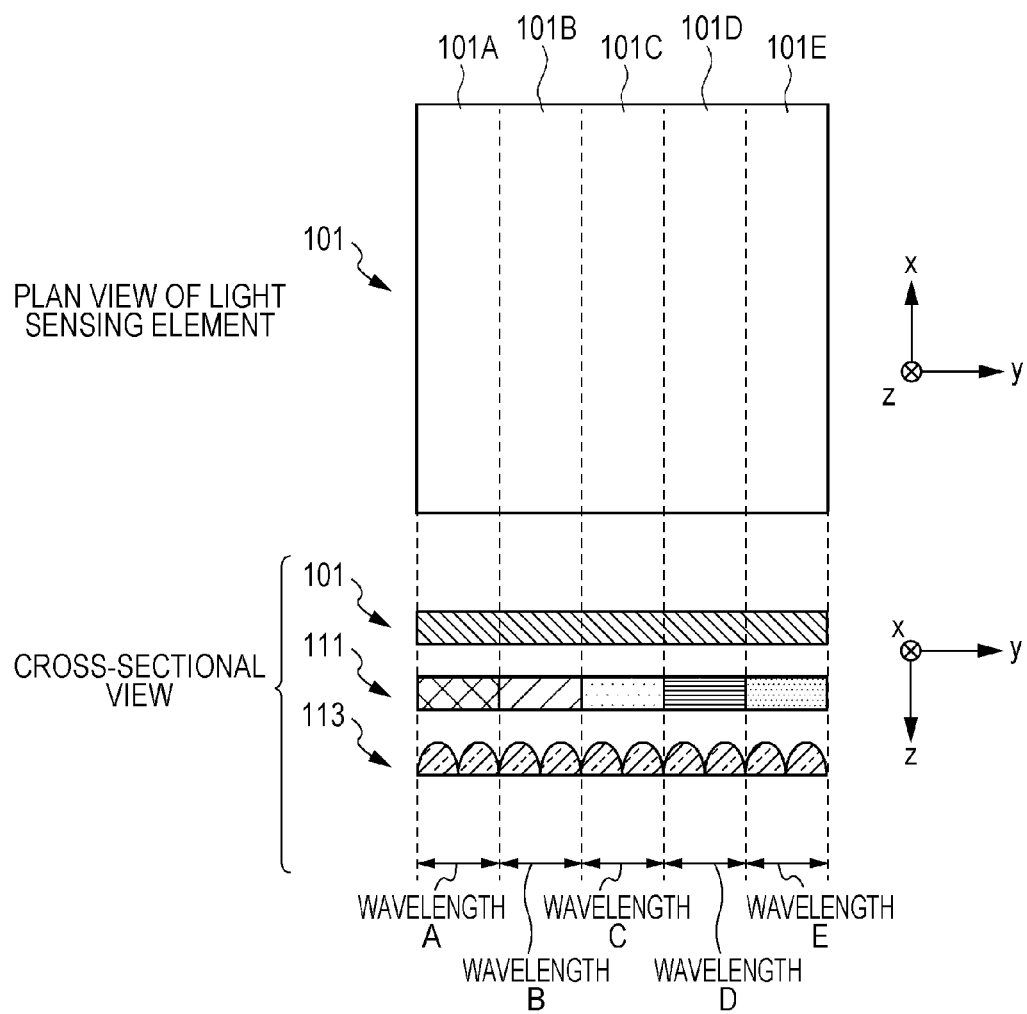
FIG. 12 is a diagram illustrating an example of an optical system included in the measurement device according to the same embodiment.

Although the upper part of FIG. 12 shows a case where the photodiode used as the light sensing element 101 is uniformly divided into five regions in a strip shape, the shape of the region is not limited to the rectangular shape as shown in FIG. 12.

Five bandpass filters are used as the optical filters 111 as shown in FIG. 12, such that light of corresponding wavelengths forms an image on the five light sensing regions. In the following description, it is assumed that the wavelength A corresponds to the central wavelength 500 nm, the wavelength B corresponds to the central wavelength 540 nm, the wavelength C corresponds to the central wavelength 580 nm, the wavelength D corresponds to the central wavelength 620 nm, and the wavelength E corresponds to the central wavelength 660 nm, respectively. In addition, the arrangement order is for convenience, and which central wavelength corresponds to a certain region may be appropriately determined.

The five optical filters 111 are disposed at the upper side (for example, directly on) of corresponding regions of the light sensing surface, as shown in the lower parts of FIGS. 10 and 12. Thereby, for example, of the white reflection light incident to the optical filter 111 provided at the directly upper side of the region 101A, only light of a predetermined width having 500 nm as the central wavelength passes through the optical filter 111, and the light of the predetermined width having 500 nm as the central wavelength forms an image on the region 101A. In addition, in FIG. 12, for convenience of illustration, although the gap between the light sensing element 101 and the optical filters 111 is shown, the optical filters 111 may be provided directly on the light sensing element 101, or may be provided with a predetermined gap.

In addition, as described above, the collimate lenses 113 for collimating the diffuse reflection light are appropriately provided at the upper side of the optical filters 111.

Here, as described with reference to FIGS. 6 to 8 in the first embodiment, the reflectance of the human skin rapidly increases around the wavelength 580 nm, and the variations in the reflectance in other wavelength bands are relatively smooth. Therefore, in order to accurately measure the reflectance at the central wavelength 580 nm, when the transmission bandwidth for each optical filter 111 is determined, the full width at half maximum of the optical filter for 580 nm is preferably smaller than the full width at half maximum of the optical filters for 500 nm, 540 nm, 620 nm, and 660 nm. Specifically, it is preferable that the full width at half maximum of the optical filter for 580 nm be 10 nm to 20 nm, and the full width at half maximum of the optical filters for 500 nm, 540 nm, 620 nm, and 660 nm be 30 nm to 50 nm.

As such, the measurement device 1 according to the embodiment has been described in detail with reference to FIGS. 10 to 12. The measurement device 1 according to the embodiment simultaneously irradiates the measurement target region with light having the same wavelength characteristic, and selects wavelengths using the optical filters provided in front of the light sensing element, thereby obtaining optical information for the measurement target placed on the measurement target region. Further, since the measurement is performed after the wavelengths distinctive to a phenomenon or a substance which is a measurement target are selected in advance, in the measurement device 1 according to the embodiment, an optical unit such as the integrating sphere or the diffraction grating is not necessary, and thereby the miniaturization of the device can be realized. Since the photodiode can be used as a light emitting element, it is possible to realize electric power conservation and a reduction in costs even in a case where 4N light emitting elements are mounted.

Application Examples of Measurement Device

Figure 13:
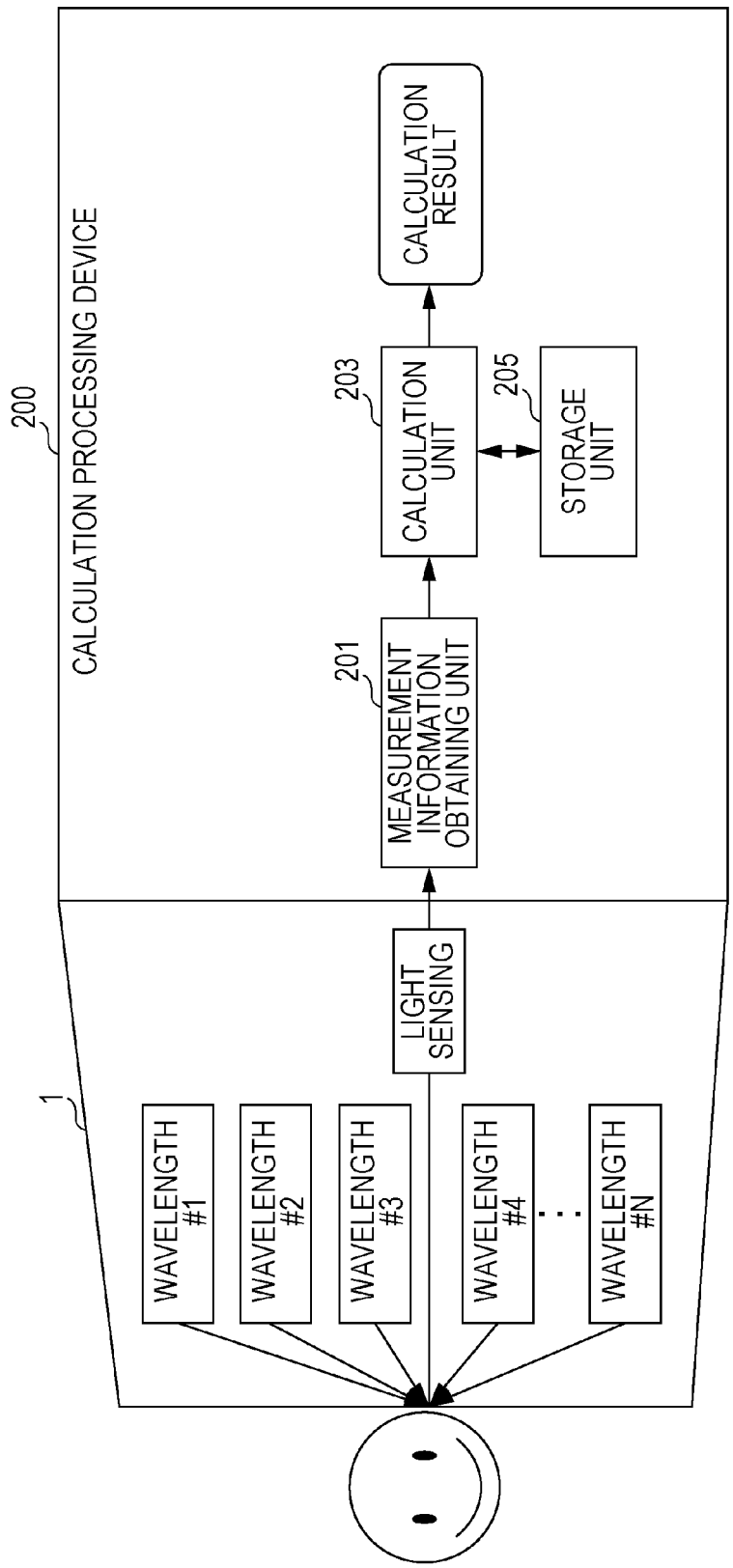
FIG. 13 is a diagram illustrating an application example of the measurement device according to each embodiment.
Figure 14:
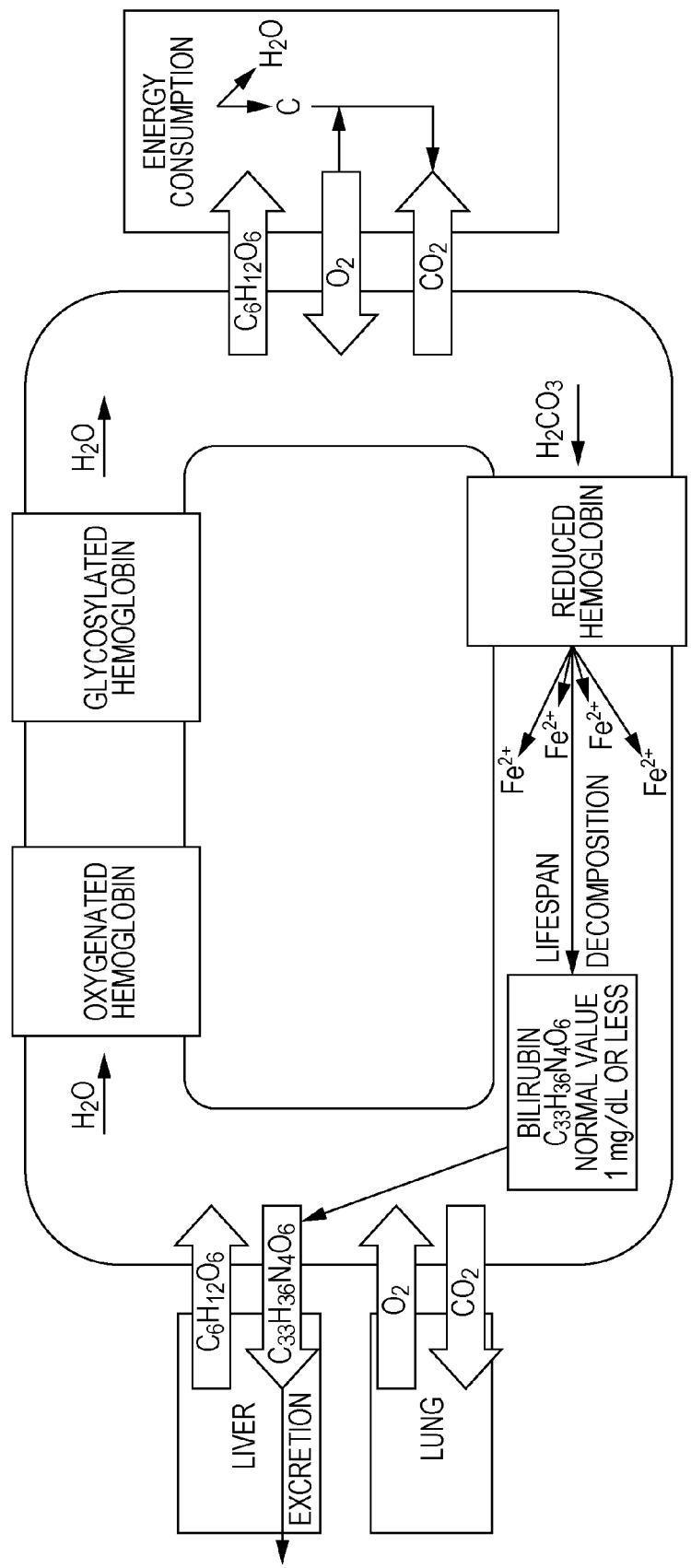
FIG. 14 is a diagram illustrating an application example of the measurement device according to each embodiment.

Next, with reference to FIGS. 13 and 14, an application example of the measurement device according to each of the embodiments will be described briefly. FIGS. 13 and 14 are diagrams illustrating application examples the measurement device according to each of the embodiments.

The measurement device 1 according to each of the embodiments is applicable to, for example, a device which measures the reflectance at a specific wavelength of human skin and evaluates the measurement result, by being used, for example, as shown in FIG. 13, in combination with a calculation processing device 200.

For example, in the example shown in FIG. 13, the measurement device 1 according to each of the embodiments irradiates the human skin with light having N wavelengths and sense reflection light from the human skin using the light sensing element 101. As a result, the light sensing element 101 generates measurement information for the sensed reflection light. The measurement device 1 outputs the measurement information generated by the light sensing element 101 to the calculation processing device 200.

A measurement information obtaining unit 201 of the calculation processing device 200 obtains the measurement information (for example, information for an arbitrary skin reflection spectrum, reflectance at a specific wavelength, or the like) generated by the measurement device 1, and outputs the measurement information to a calculation unit 203.

The calculation unit 203 performs calculation using the measurement information obtained by the measurement information obtaining unit 201 based on the Lambert-Beer law or the like, and calculates the abundance of various kinds of substances which are present inside human skin.

Human skin has a layered structure of epidermis, dermis, and subcutaneous from a place close to the surface of the body. In addition, by using reflection light where light is provided to the human skin and is reflected by the interface between the epidermis and dermis, it is possible to measure the abundance or the concentration of hemoglobin or the like present in capillaries.

The Lamberto-Beer law indicates that the concentration of a substance is proportional to the absorbance obtained from the measurement result, and the absorbance is defined as a common logarithm of a reciprocal number of measured transmittance. In addition, since the absorbance can be indicated by a product of an absorbance coefficient unique to a substance and an amount of the substance, finally, the physical quantity can be calculated using the following Equation 101.

$$\text{Physical quantity} = \text{Log}(1/\text{transmittance})/\text{absorbance coefficient} \quad (101)$$

Therefore, the calculation unit 203 calculates the abundance or concentration of a noted substance based on the result measured by the measurement device 1, Equation 101, and the like.

The calculation processing device 200 can provide transition of a daily measurement result regarding a contained substance of interest to a user by displaying the result calculated by the calculation unit 203 on a display or the like.

FIG. 14 is a schematic diagram illustrating hemoglobin metabolism inside the human body.

Hemoglobin is a generic name of protein including four subunits present in blood. As shown in FIG. 14, hemoglobin is changed to oxygenated hemoglobin through binding with oxygen absorbed from the lungs, and is changed to reduced hemoglobin through reaction with carbon dioxide after extricating the oxygen to each place inside the body. In addition, if a monosaccharide such as glucose is extricated from the liver into the blood, the hemoglobin becomes glycosylated hemoglobin through binding with the monosaccharide. The glycosylated hemoglobin is changed to reduced hemoglobin after extricating the bonded monosaccharide to each place inside the body. The extricated oxygen and monosaccharide are consumed as energy in each place inside the body. In addition, when the reduced hemoglobin reaches the end of its lifespan, it is decomposed into the compound ($C_{33}H_{36}N_4O_6$) called bilirubin, is metabolized in the liver, and is excreted out of the body.

Here, since the oxygenated hemoglobin, the glycosilated hemoglobin, the reduced hemoglobin, and the like which are present in the metabolism path absorb light of slightly different wavelengths, the concentration thereof in the blood can be measured by paying attention to a specific wavelength of the reflection light. The five wavelengths of 500 nm, 540 nm, 580 nm, 620 nm, and 660 nm shown in the first and second embodiments function as wavelength bands useful to measure the substance amount of these types of hemoglobin. Therefore, it is possible to calculate the abundance or the concentration of the oxygenated hemoglobin, the glycosilated hemoglobin, and the reduced hemoglobin by measuring the reflectance at the five wavelengths described above, using the measurement device 1 according to each of the embodiments. By providing the abundance of the contained substances to a user, the user can perform purposeful health management or monitor health problems.

Although the preferred embodiments have been described with reference to the accompanying drawings, the present application is not limited to the embodiments. It is understood by those skilled in the art that various modifications and alterations apparently occur within the scope of the appended claims, and they are naturally included in the technical scope.

For example, in the embodiments, although light of a low numerical aperture (for example, NA=about 0.2) is radiated by the light emitting elements, light radiated by the light emitting elements may be used after being changed to parallel light.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A measurement device comprising:
   a light sensing element on which light from a measurement target region placing a measurement target thereon forms an image; and
   a plurality of light emitting elements that are disposed around the light sensing element in a ring shape and radiate light to the measurement target region,
   wherein the plurality of light emitting elements are disposed to be tilted with respect to the normal line of the measurement target region such that the central line of radiated emission from each of the light emitting elements passes through a substantial center of the measurement target region,
   wherein an angle formed by the central line of the radiated emission and the normal line of the measurement target region is set according to a separation distance between the measurement target region and the light sensing element.

2. The measurement device according to claim 1, wherein if the separation distance is equal to or less than a predetermined threshold value, the angle is set to 45°, and if the separation distance exceeds the predetermined threshold value, the angle is set to be less than 45°.

3. The measurement device according to claim 1, wherein the measurement target region is provided to face the light sensing element.

4. The measurement device according to claim 1, wherein 4N (where N is an integer equal to or more than 1) light emitting elements are disposed around the light sensing element at an interval of (90/N)°.

5. The measurement device according to claim 4, wherein the light emitting elements which radiate light having different N wavelengths are disposed by four for each wavelength as the plurality of light emitting elements.

6. The measurement device according to claim 5, wherein twenty light emitting elements which radiate light having different 5 wavelengths are disposed around the light sensing element at an interval of 18°.

7. The measurement device according to claim 6, wherein the light having the different 5 wavelengths has 500 nm, 540 nm, 580 nm, 620 nm, and 660 nm, respectively, as a central wavelength.

8. The measurement device according to claim 7, wherein the full width at half maximum of the light having 580 nm as the central wavelength is smaller than the full width at half maximum of the light having 500 nm, 540 nm, 620 nm, and 660 nm as the central wavelength.

9. The measurement device according to claim 5, wherein the light emitting elements which radiate the light having the different N wavelengths radiate the light in a time divisional manner so as to have a predetermined pulse width using N pulses.

10. The measurement device according to claim 5, wherein each light emitting element radiates a light of different wavelength from adjacent light emitting elements.

11. The measurement device according to claim 1, wherein a numerical aperture of the radiated emission which is provided to the measurement target region is equal to or less than 0.2.

12. The measurement device according to claim 1, wherein the plurality of light emitting elements radiate light having the same wavelength characteristic.

13. The measurement device according to claim 12, wherein the plurality of light emitting elements respectively and simultaneously radiate white light so as to have a predetermined pulse width.

14. The measurement device according to claim 12, wherein a light sensing surface of the light sensing element is divided into N regions, and
wherein an optical filter which transmits light having different N wavelengths therethrough is provided at an upper side of each of the regions.

15. The measurement device according to claim 14, wherein the light sensing surface of the light sensing element is divided into five regions, and
wherein the optical filters transmit light having 500 nm, 540 nm, 580 nm, 620 nm, and 660 nm as a central wavelength therethrough.

16. The measurement device according to claim 15, wherein the full width at half maximum of the light having 580 nm as the central wavelength is smaller than the full width at half maximum of the light having 500 nm, 540 nm, 620 nm, and 660 nm as the central wavelength.

17. The measurement device according to claim 15, wherein collimated diffuse reflection from the measurement target region is incident to the optical filters.

18. The measurement device according to claim 1, wherein the size of the measurement target region is substantially the same as the size of a spot formed by light radiated from the plurality of light emitting elements.

19. The measurement device according to claim 1, wherein the measurement device is disposed inside a casing at which an opening portion is provided, and
wherein the measurement target region is a human skin surface placed on the opening portion.

20. The measurement device according to claim 1, wherein light sensed by the light sensing element is used to generate measurement information including at least one of information for a skin reflection spectrum and reflectance at a specific wavelength.

21. The measurement device according to claim 1, wherein said angle is substantially the same for each of the plurality of the light emitting elements.

22. A measurement method comprising:
radiating light of a predetermined wavelength from a plurality of light emitting elements which are disposed around a light sensing element in a ring shape on which light from a measurement target region placing a measurement target thereon forms an image, and which radiate light to the measurement target region, such that the central line of radiated emission from each of the light emitting elements passes through a substantial center of the measurement target region, wherein an angle formed by the central line of the radiated emission and the normal line of the measurement target region is set according to a separation distance between the measurement target region and the light sensing element; and
causing the light sensing element to sense diffuse reflection light from the measurement target region.

* * * * *